(12) United States Patent
Roberts

(10) Patent No.: US 8,542,797 B2
(45) Date of Patent: Sep. 24, 2013

(54) RADIOTHERAPY APPARATUS CONFIGURED TO TRACK A MOTION OF A TARGET REGION USING A COMBINATION OF A MULTILEAF COLLIMATOR AND A PATIENT SUPPORT

(75) Inventor: David Anthony Roberts, South Croydon (GB)

(73) Assignee: Elekta AB (Publ), Stockholm (SE)

( * ) Notice: Subject to any disclaimer, the term of this patent is extended or adjusted under 35 U.S.C. 154(b) by 318 days.

(21) Appl. No.: 12/889,898

(22) Filed: Sep. 24, 2010

(65) Prior Publication Data

US 2012/0076269 A1    Mar. 29, 2012

(51) Int. Cl.
*A61N 5/10* (2006.01)
(52) U.S. Cl.
USPC .......................................................... 378/65
(58) Field of Classification Search
USPC ...................................... 378/65, 68
See application file for complete search history.

(56) References Cited

U.S. PATENT DOCUMENTS

| | | | |
|---|---|---|---|
| 7,916,840 B2* | 3/2011 | Noguchi | 378/150 |
| 8,042,209 B2* | 10/2011 | D'Souza et al. | 5/610 |
| 8,229,068 B2* | 7/2012 | Lu et al. | 378/65 |
| 2012/0043481 A1* | 2/2012 | Mansfield et al. | 250/492.1 |

* cited by examiner

*Primary Examiner* — Allen C. Ho
(74) *Attorney, Agent, or Firm* — Sunstein Kann Murphy & Timbers LLP

(57) ABSTRACT

The present invention provides a radiotherapy apparatus for applying therapeutic radiation to a target region of a patient, comprising a patient support, a source of radiation, a collimator comprising a plurality of leaves, a sensing system and control circuitry. The position of a target region is determined and resolved into two components orthogonal to the radiation beam axis. One component is assigned to the patient support, and the other to the collimator leaves, such that movement of the target region is compensated for and the radiation beam intersects is correctly targeted.

13 Claims, 3 Drawing Sheets

RADIOTHERAPY APPARATUS CONFIGURED TO TRACK A MOTION OF A TARGET REGION USING A COMBINATION OF A MULTILEAF COLLIMATOR AND A PATIENT SUPPORT

FIELD OF THE INVENTION

The present invention relates to radiotherapy, and particularly relates to a method and apparatus for radiotherapy in which the motion of a target, such as due to the respiratory cycle for example, is tracked during treatment.

BACKGROUND ART

It is known that exposure of human or animal tissue to ionizing radiation will kill the cells thus exposed. This finds application in the treatment of pathological cells, for example. In order to treat tumors deep within the body of the patient, the radiation must however penetrate the healthy tissue in order to irradiate and destroy the pathological cells. In conventional radiation therapy, large volumes of healthy tissue can thus be exposed to harmful doses of radiation, resulting in prolonged recovery periods for the patient. It is, therefore, desirable to design a device for treating a patient with ionizing radiation and treatment protocols so as to expose the pathological tissue to a dose of radiation which will result in the death of those cells, whilst keeping the exposure of healthy tissue to a minimum.

Several methods have previously been employed to achieve the desired pathological cell-destroying exposure whilst keeping the exposure of healthy cells to a minimum. Many methods work by directing radiation at a tumor from a number of directions, either simultaneously from multiple sources or multiple exposures from a single source. The intensity of radiation emanating from each direction is therefore less than would be required to actually destroy cells (although still sufficient to damage the cells), but where the radiation beams from the multiple directions converge, the intensity of radiation is sufficient to deliver a therapeutic dose. By providing radiation from multiple directions, the amount of radiation delivered to surrounding healthy cells can be minimized.

Of course it is also important that the radiation should be accurately targeted on the region that requires treatment. For this reason, patients are required to remain still for the duration of the therapy session, to minimize the risk of damage to healthy tissue surrounding the target region. However, some movement is inevitable, e.g. through breathing, or other involuntary movements.

A number of different techniques for the tracking of moving targets in radiotherapy are known. Many involve tracking the target by moving the leaves of the multi-leaf collimator (MLC), as described in U.S. Pat. Nos. 7,469,035 and 7,221,733. Others make use of a moveable patient support, such as in US patent application number 2008/0212737, or the Applicant's own US patent application number 2009/0168961, now U.S. Pat. No. 8,042,209. Tracking systems involving only motion of the couch or MLC leaves place high demands on the chosen device, and limit the degrees of freedom that can be used to track the target movement.

There has also been an attempt to use motion of the MLC leaves and the patient support in unison, as described in a paper by Podder et al ("Co-ordinated dynamics-based control of robotic couch and MLC-bank for feedforward radiation therapy", The International Journal of Computer Assisted Radiology and Surgery, Vol. 2, pp. S106-S108). The "division of labour" between the two is based on the frequencies of the individual movements that make up the target trajectory. The movement of the target region is broken down into low- and high-frequency components, which can then be tracked by the patient couch and MLC leaves respectively. However, this approach is complex.

SUMMARY OF THE INVENTION

The proposed invention is a vastly simplified method of deconstructing the motion of a target region so that it can be tracked between the movement of the patient couch and the MLC leaves. In brief, the motion is broken down into two orthogonal axes. One of these axes is assigned to the couch, the other to the MLC. For example, in the case of a tumor which follows an elliptical path, the major axis, which represents the largest range of motion, may be assigned to the MLC, and the minor axis, with the smallest range of motion, would be assigned to the couch. In this way, as the target precesses around its motion path, the combination of the two movement means allows the target to be tracked more efficiently than by either in isolation, and with a method that is simpler to implement than trying to perform frequency analysis on the motion of the target. It reduces the mechanical requirements on the couch, as there is no need to move the patient as much or as quickly as is required with couch tracking alone. It also means the MLC tracking can be optimised, as the MLC can be oriented to track the target in one axis only, which is less demanding on the leaf control than trying to track a target that is moving both across and along the MLC leaf range.

Thus, in a first aspect of the present invention, there is provided a radiotherapy apparatus for applying therapeutic radiation to a target region of a patient, comprising a patient support, a source of radiation, a collimator comprising a plurality of leaves, a sensing system and control circuitry. The position of a target region is determined and resolved into two components orthogonal to the radiation beam axis. One component is assigned to the patient support, and the other to the collimator leaves, such that movement of the target region is compensated for and the radiation beam intersects is correctly targeted.

The first and second components may be orthogonal to one another, but this is not essential.

The apparatus is particularly useful in tracking cyclical motion of a target, but may be used to track other types of motion as well. For example, such cyclical motion may be elliptical. In that case, the component assigned to the couch motion can be parallel to the minor axis of the ellipse, and the component assigned to the MLC leaves parallel to the major axis of the ellipse. In non-elliptical target movement, the component with the greatest range of motion may nonetheless be assigned to the MLC leaves, and the component with the smallest range of motion assigned to the couch. Alternatively, the reverse or another configuration could be adopted.

The MLC may be rotatable about an axis parallel to the radiation beam axis, so that the MLC leaves can be aligned with the second component (i.e. "aligned" in the sense that they are moveable into and out of the radiation beam in that direction).

The sensing system may be a CT imaging apparatus, although alternatives may also be considered by those skilled in the art.

In one embodiment, movement of the couch is enabled by means of a hexapod, which allows movement with up to six degrees of freedom.

In a second aspect of the invention, there is provided a method of treating a patient by radiotherapy, in which a radiotherapy apparatus comprises a patient support, on which the patient is positioned for treatment, a source of radiation, arranged to emit a beam of radiation along an axis towards the patient, and a collimator comprising a plurality of leaves, moveable into the radiation beam in order to delimit the extent of the radiation beam. The method comprises the steps of determining the position of a target region in the patient; resolving said position into a first component in a first direction orthogonal to the radiation beam axis, and a second component in a second direction orthogonal to the radiation beam axis; and moving the patient support in the first direction according to the first component, and the collimator leaves in the second direction according to the second component, such that the radiation beam intersects the target region.

The leaves of the collimators that can be used in this invention are typically mounted on dynamic leaf guides. Movement of the leaves can be effected either by movement of the individual leaves relative to the leaf guide on which it is (and other leaves are) mounted, or by movement of the leaf guide relative to the radiation head or other mounting on which it is supported. Normally, gross movement of the leaves in bulk is achieved by movement of the leaf guide whereas fine adjustment and shaping of the beam is achieved by movement of the leaves. In this case, either option may be suitable depending on the nature of the leaf movement needed.

BRIEF DESCRIPTION OF THE DRAWINGS

An embodiment of the present invention will now be described by way of example, with reference to the accompanying figures in which.

DETAILED DESCRIPTION OF THE EMBODIMENTS

As discussed above, accurate direction of a radiation beam towards a target region of a patient is crucially important for radiotherapy. The more accurately a therapeutic radiation beam can be directed towards the target for therapy (e.g. a tumor), the less damage is inflicted on surrounding healthy tissue and potentially sensitive anatomical structures. This is complicated by the fact that, in general, the target will not be stationary during treatment. Movement of the patient can be minimised through appropriate restraints or sedation. However, the internal organs of the patient nonetheless undergo movement due to the cardiac and/or respiratory cycles.

Figure 1:
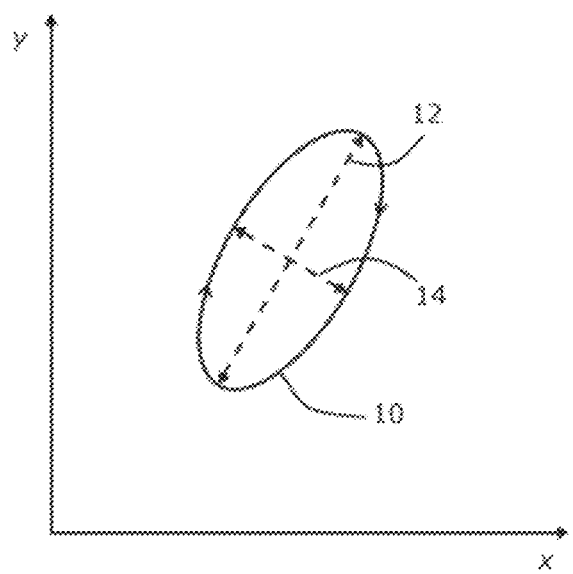
FIG. 1 shows a beam's eye view of the motion of a target region undergoing cyclic elliptical motion.

FIG. 1 is a schematic diagram showing the motion of a target due to these cycles, as seen from a radiation beam's point of view. That is, the motion shown in FIG. 1 is a projection of the three-dimensional motion of the target into a plane orthogonal to the radiation beam axis. The locus of motion of the target is shown by the solid line 10. In the illustrated example, this motion is elliptical, with a major axis 12 and a minor axis 14. Indeed, in an idealized case, the three-dimensional cyclical motion will generally be elliptical. Thus, when projected into a plane perpendicular to the radiation beam axis, the motion is still elliptical.

According to embodiments of the present invention this projected motion is resolved into two components, with each component of motion assigned to a different part of the radiotherapy apparatus: one component assigned to the leaves of a collimator, and the other assigned to motion of a patient support. Thus, the collimator leaves compensate for motion of the target in a first direction, and the patient support compensates for motion of the target in a second direction. This simple division of motion between apparatus components allows the radiation beam to accurately track motion of the target without unnecessarily complicating the task.

Figure 2:
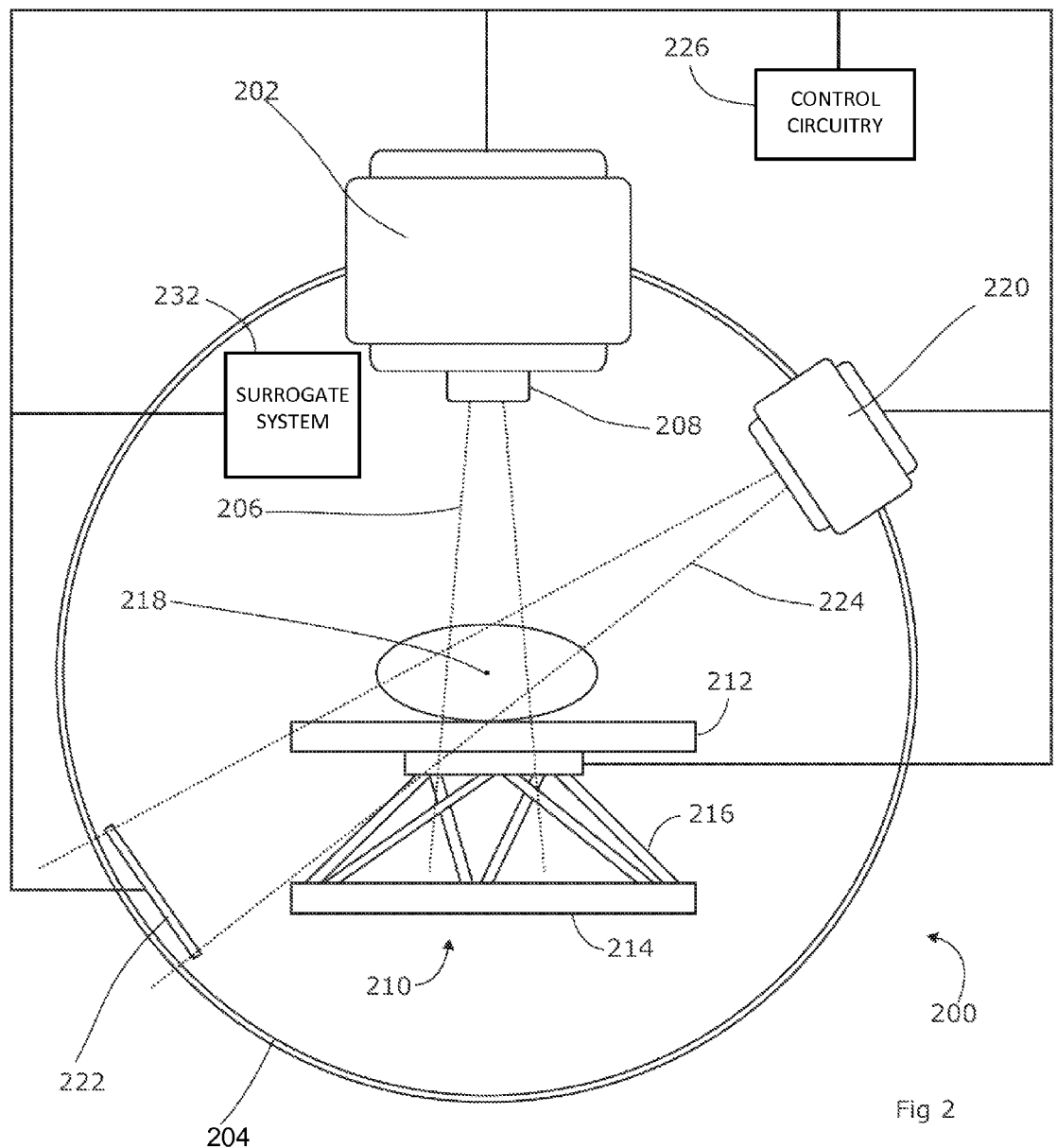
FIG. 2 shows a radiotherapy system according to embodiments of the present invention.

FIG. 2 is a schematic drawing of an apparatus 200 for performing radiotherapy according to embodiments of the present invention.

The apparatus comprises a source of therapeutic radiation 202, mounted on a rotatable gantry 204. The radiation produced by the source 202 may be x-rays, electrons, or any other radiation suitable for the purpose of therapeutic treatment. The source produces a collimated radiation beam 206 which is directed generally to intersect with the axis of rotation (or isocentre 218) of the gantry 204; some offset from the isocentre may be allowed in certain modes of treatment, however.

A multi-leaf collimator (MLC) 208 is coupled to the radiation source 202 in order to collimate and direct the radiation beam 206. The MLC 208 comprises at least two opposing banks of leafs, which extend in parallel directions and from opposite sides into the radiation beam. The leaves may be controlled to take up any position in a continuous range of positions from completely outside the radiation beam (and therefore allowing the radiation in that plane through without interruption) to completely crossing the radiation beam (and therefore completely blocking the radiation in that plane). The MLC 208 is rotatable about an axis parallel to the radiation beam 206.

The radiotherapy system 200 further comprises a patient support 210, for supporting a patient undergoing treatment. The support 210 is generally aligned along the rotation axis of the gantry 204. However, it may be able to rotate away from that axis. The support 210 comprises a couch 212, on which the patient rests, and a base 214. Coupled between the two is a hexapod 216 (also known as a "Stewart platform"), which is controllable to adjust the position of the couch 212 with respect to the base 214 with up to six degrees of freedom (x, y, z, pitch, roll and yaw).

Those skilled in the art will appreciate that the drawing in FIG. 2 is schematic, and not a strictly accurate depiction of the radiotherapy system as it may be put into use. For example, the patient support 210, including hexapod 216, may not fit entirely within the gantry 204 as shown. Rather, the gantry 204 may comprise a "C-arm" which carries the source of radiation 202 and other equipment around the support 210.

An x-ray source 220 is also mounted to the gantry 204 and is arranged to project a wide beam 224 of radiation generally directed towards the isocentre 218 of the patient. The wide beam of radiation 224 is at a relatively low energy, suitable for imaging purposes (i.e. keV as opposed to the MeV of the therapeutic source 202).

A two-dimensional flat-panel detector 222 is also mounted on the gantry 204, opposite the source 220 and arranged to rotate in synchronism therewith. If the support includes a C-arm then this can be achieved by mounting the detector on the opposite arm.

Thus, radiation emitted by the source 220 is partially absorbed by the patient and the attenuated radiation is detected by the flat panel detector 222. The source 220 and detector 222 are then indexed rotationally and a fresh image obtained. This is repeated until sufficient images are acquired to reconstruct the volume data, typically one complete rotation.

The apparatus further comprises cables linking the sources 202, 220, detector 222 and rotational gantry 204 to control circuitry 226 which processes the data generated including the images, source intensity (etc), and rotational support position. Data is output via any suitable means, depicted generally as a monitor but not limited thereto, and the system is controlled by any suitable input means.

Respiration correlation techniques may be applied to the acquired projection images by the control circuitry 224.

In the illustrated embodiment, a surrogate signal acquisition system 232 is provided to assist in this process. Various surrogate signals may be used, and all are within the scope of the present invention. Examples include the Varian RPM system, in which an external marker on the surface of the patient is monitored by a camera, the Vision RT camera-based surface tracking system, the Accuracy system using a marker vest and cameras, and our use of a pressure sensor in the abdominal compression plate (see WO2008/040379). The surrogate signal will usually be one having a low latency, to allow it to be used for gating the radiation beam or tracking the target position.

Various methods may be used to combine the imaging information obtained via the imaging radiation source 220 and the detector 222, and the signal from the surrogate system 232. One method is set out in co-pending PCT application number PCT/EP2008/010396, US Patent Application Pub. No. 2011/0243387 A1, the entire contents of which are incorporated herein by reference. In that method, each two-dimensional CT image has a corresponding surrogate signal value acquired at the same time as the image. The images are then analysed to determine their phase within the cardiac/respiratory cycle. Images having a similar phase are then grouped together, and a mean average taken of their respective surrogate signal values. Thus a relationship is established between the value of the surrogate signal and the phase of cycle (and therefore the position of the target). The instantaneous surrogate signal value can then be used to determine the phase within the cycle and the location of the target within the patient.

In embodiments of the present invention, the location of the target may be tracked by implanting markers into the target region. For example, the markers may emit an electromagnetic signal which is trackable with an appropriate detector. Alternatively, the markers may be metallic and thus show up more clearly in CT or other images of the target region.

The control circuitry 226 can therefore measure and track the location of the target throughout its cyclic motion. According to embodiments of the present invention, this location is resolved into two components in a plane orthogonal to the radiation beam axis. In one embodiment, the two components may also be orthogonal to one another; however, this is not a requirement.

The control circuitry 226 further controls motion of the couch 212 (via the hexapod 216) and the orientation and positioning of the MLC leaves on the basis of the two components. One component is assigned to the MLC leaves and one to the couch motion.

In one embodiment, the control circuitry 226 determines the direction in which the greatest range of motion occurs, and assigns the corresponding component to the MLC leaves. The direction in which the smallest range of motion occurs may be assigned to the motion of the couch. The couch has a greater inertia than the MLC leaves, due to its own weight and that of the patient. By assigning the component with the smallest range of motion (and therefore the slowest movement to the motion of the couch), synchronization of the couch movement with motion of the target region is made easier and patient discomfort due to motion of the couch is minimized.

Figure 3:
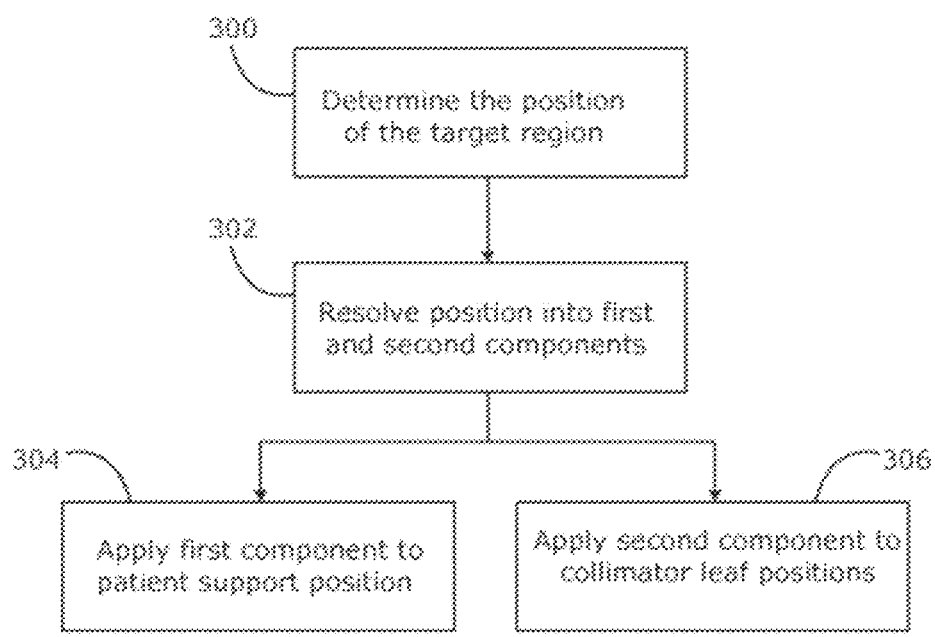
FIG. 3 is a flowchart of a method according to embodiments of the present invention.

FIG. 3 is a flowchart of a method in accordance with embodiments of the present invention.

In step 300, the position of the target region is determined. Various methods have been discussed above for this purpose.

In step 302, the control circuitry 226 resolves this position into first and second components in a plane orthogonal to the axis of the radiation beam (i.e. first and second components in the beam's eye view, cf FIG. 1). These components may be orthogonal or at an arbitrary angle to one another. It will be apparent to those skilled in the art that any component of position in a direction parallel to the radiation beam axis is unimportant for the positioning of the MLC leaves and the couch (see below), as the radiation beam travels in a straight line in that direction. Of course, the component of position parallel to the radiation beam may have to be taken into consideration for other purposes. For example, if the radiation beam is formed from particles such as electrons or, particularly, protons, the dose will be affected by the amount of tissue the radiation has to pass through to reach the target, i.e. its "depth". This may have consequences in treatment planning and the required dose rate, but will not generally affect the positioning of the MLC leaves or the couch as described below.

The method then splits into two parallel steps 304 and 306, which are performed simultaneously. In step 304, the first component is assigned to the patient support 210, whose position is controlled by the control circuitry 226 and the hexapod 216 to compensate for the first component of the position of the target region. That is, by repeatedly updating the position of the couch, the movement of the couch 212 substantially cancels movement of the target region in the direction of the first component, such that there is no movement in that direction relative to the position of the radiation source 202. As previously described, the hexapod 216 has six degrees of freedom, and so movement of the target can be tracked in essentially any direction.

In step 306, the second component is assigned to the MLC leaves 208, whose position is controlled by the control circuitry 226 to compensate for the second component of the position of the target region. That is, by repeatedly updating the position of the MLC leaves, the movement of the MLC leaves tracks movement of the target region in the direction of the second component, such that the therapeutic radiation beam 206 tracks the motion of the target in that direction. The MLC 208 itself may be rotated in order to align the leaves with the second component.

It can thus be seen that the action of the couch motion is to collapse the movement of the target to a single direction relative to the radiation source. This movement up and down a single direction may be easily tracked by appropriate movement of the MLC leaves.

The above description has focussed on a resolution of the target position from the perspective of a single viewpoint around the patient. However, it can be seen that this principle may be extended to apply from substantially any position around the patient (i.e. any angle of rotation of the gantry 204). The plane of motion of the couch 212 may be continuously adjusted to be orthogonal to the radiation beam axis.

The present invention therefore describes a method and an apparatus for tracking the motion of a target region during radiotherapy. The motion is resolved into two components orthogonal to the radiation beam axis. One component is assigned to motion of the couch, where it is compensated, and the other assigned to the MLC leaves, which adjust the radiation beam to track the target motion in that direction. The invention thus provides an elegant solution to the division of labour between different components of the radiotherapy system, allowing a target to be tracked with a degree of ease not found in conventional systems.

It will of course be understood that many variations may be made to the above-described embodiment without departing from the scope of the present invention.

The invention claimed is:

1. A radiotherapy apparatus for applying therapeutic radiation to a target region of a patient, the apparatus comprising:
    a patient support, on which the patient is positioned for treatment;
    a source of radiation, arranged to emit a beam of radiation along an axis towards the patient;
    a collimator comprising a plurality of leaves, moveable into the radiation beam in order to delimit an extent of the radiation beam;
    a sensing system, configured to determine a position of a target region; and
    control circuitry, configured to resolve said position into a first component in a first direction orthogonal to the radiation beam axis and a second component in a second direction orthogonal to the radiation beam axis, and to control the patient support to move in the first direction according to the first component, and the plurality of collimator leaves to move in the second direction according to the second component, such that the radiation beam intersects the target region.

2. A radiotherapy apparatus as claimed in claim 1, wherein the first component is orthogonal to the second component.

3. A radiotherapy apparatus as claimed in claim 1, wherein the target region undergoes cyclical motion, and wherein the patient support and the plurality of collimator leaves move such that the radiation beam tracks said cyclical motion.

4. A radiotherapy apparatus as claimed in claim 3, wherein said cyclical motion comprises substantially elliptical motion in a plane orthogonal to the radiation beam axis, and wherein the first direction is parallel to a minor axis of the elliptical motion, and the second direction is parallel to a major axis of the elliptical motion.

5. A radiotherapy apparatus as claimed in claim 1, wherein said collimator is rotatable about an axis parallel to the radiation beam axis.

6. A radiotherapy apparatus as claimed in claim 1, wherein said sensing system comprises a CT imaging system.

7. A radiotherapy apparatus as claimed in claim 1, wherein said patient support comprises a hexapod for adjusting a position of the patient support.

8. A method of treating a patient by radiotherapy, in which a radiotherapy apparatus comprises a patient support, on which the patient is positioned for treatment, a source of radiation, arranged to emit a beam of radiation along an axis towards the patient, and a collimator comprising a plurality of leaves, moveable into the radiation beam in order to delimit the extent of the radiation beam, the method comprising:
    determining a position of a target region in the patient;
    resolving said position into a first component in a first direction orthogonal to the radiation beam axis, and a second component in a second direction orthogonal to the radiation beam axis; and
    moving the patient support in the first direction according to the first component, and the plurality of collimator leaves in the second direction according to the second component, such that the radiation beam intersects the target region.

9. A method as claimed in claim 8, wherein the first component is orthogonal to the second component.

10. A method as claimed in claim 8, wherein the target region undergoes cyclical motion, and wherein the patient support and the plurality of collimator leaves move such that the radiation beam tracks said cyclical motion.

11. A method as claimed in claim 10, further comprising:
    determining an axis along which the largest range of motion of the target region occurs; and
    rotating the collimator about an axis parallel to the radiation beam axis, such that said second direction is aligned with said axis along which the largest range of motion of the target region occurs.

12. A method as claimed in claim 10, wherein said cyclical motion comprises substantially elliptical motion in a plane orthogonal to the radiation beam axis, and wherein the first direction is parallel to a minor axis of the elliptical motion, and the second direction is parallel to a major axis of the elliptical motion.

13. A method as claimed in claim 8, wherein said patient support comprises a hexapod for adjusting a position of the patient support.

* * * * *